(12) United States Patent
Reddy

(10) Patent No.: US 9,268,907 B2
(45) Date of Patent: Feb. 23, 2016

(54) SYSTEM AND METHOD FOR AUTOMATICALLY MODIFYING SOURCE CODE TO ACCOMMODATE A SOFTWARE MIGRATION

(71) Applicant: SYNTEL, INC., Troy, MI (US)

(72) Inventor: Murlidhar Reddy, Maharashtra (IN)

(73) Assignee: Syntel, Inc., Troy, MI (US)

( * ) Notice: Subject to any disclaimer, the term of this patent is extended or adjusted under 35 U.S.C. 154(b) by 0 days.

(21) Appl. No.: 14/306,026

(22) Filed: Jun. 16, 2014

(65) Prior Publication Data

US 2014/0372976 A1    Dec. 18, 2014

Related U.S. Application Data

(60) Provisional application No. 61/834,908, filed on Jun. 14, 2013.

(51) Int. Cl.
  *G06F 9/44*    (2006.01)
  *G06F 19/00*   (2011.01)
  *G06Q 50/22*   (2012.01)

(52) U.S. Cl.
  CPC ............... *G06F 19/328* (2013.01); *G06F 8/30* (2013.01); *G06F 8/70* (2013.01); *G06Q 50/22* (2013.01); *G06F 19/322* (2013.01)

(58) Field of Classification Search
  CPC .............................................. G06F 8/00–8/38
  USPC .................. 717/110–123, 168–178
  See application file for complete search history.

(56) References Cited

U.S. PATENT DOCUMENTS

| | | | |
|---|---|---|---|
| 4,558,413 A | 12/1985 | Schmidt et al. | |
| 6,493,871 B1 | 12/2002 | McGuire et al. | |
| 7,233,938 B2 | 6/2007 | Carus et al. | |
| 7,437,302 B2 | 10/2008 | Haskell et al. | |
| 7,546,595 B1 | 6/2009 | Wickham et al. | |
| 7,861,239 B2 | 12/2010 | Mayfield et al. | |
| 8,370,799 B2 * | 2/2013 | Nir-Buchbinder et al. ... | 717/110 |
| 2003/0191665 A1 | 10/2003 | Fitzgerald et al. | |
| 2005/0137912 A1 | 6/2005 | Rao et al. | |
| 2008/0195999 A1 | 8/2008 | Cohen et al. | |

(Continued)

OTHER PUBLICATIONS

Stein, Brian D., et al. "The validity of International Classification of Diseases, Ninth Revision, Clinical Modification diagnosis codes for identifying patients hospitalized for COPD exacerbations." CHEST Journal 141.1 (2012), pp. 87-93.*

(Continued)

*Primary Examiner* — Satish Rampuria
(74) *Attorney, Agent, or Firm* — Dykema Gossett PLLC

(57) ABSTRACT

A system for automatically modifying source code to accommodate a software migration receives a software codebase a software codebase that supports international classification of diseases, ninth revision (ICD-9) codes and that contains a plurality of lines of source code, receives a codebase impact assessment report identifying each impacted line of the plurality of lines of source code in the codebase, each impacted line requiring modification in order to support migration from ICD-9 codes to international classification of diseases, tenth revision (ICD-10) codes, and automatically modifies the codebase by modifying each impacted line of source code identified in the codebase impact assessment report so that the modified codebase supports migration from ICD-9 codes to ICD-10 codes.

18 Claims, 19 Drawing Sheets

(56) References Cited

U.S. PATENT DOCUMENTS

| | | |
|---|---|---|
| 2009/0150181 A1 | 6/2009 | Gejdos et al. |
| 2009/0164252 A1 | 6/2009 | Morris et al. |
| 2010/0094657 A1 | 4/2010 | Stern et al. |
| 2010/0198799 A1* | 8/2010 | Krishnan et al. ............... 707/702 |
| 2012/0078979 A1 | 3/2012 | Ghimire |
| 2012/0089964 A1 | 4/2012 | Sawano |
| 2012/0311426 A1 | 12/2012 | Desai et al. |
| 2013/0144651 A1* | 6/2013 | Rao .................................... 705/3 |
| 2013/0185094 A1* | 7/2013 | Mukerji et al. ................... 705/3 |
| 2013/0227524 A1 | 8/2013 | Im et al. |
| 2013/0227533 A1* | 8/2013 | Tonkin et al. ................. 717/137 |

OTHER PUBLICATIONS

McDonald, Clement J., et al. "Open Source software in medical informatics—why, how and what." International journal of medical informatics 69.2 (2003), pp. 175-184.*

Ayewah, Nathaniel, et al. "Evaluating static analysis defect warnings on production software." Proceedings of the 7th ACM SIGPLAN-SIGSOFT workshop on Program analysis for software tools and engineering. ACM, 2007, pp. 1-7.*

* cited by examiner

EXCEL

| A | B | C | D | E | F | G | H | I | J |
|---|---|---|---|---|---|---|---|---|---|
| LIB. NAME | COMP. NAME | COMP. TYPE | FILE NAME | IT R # | LN # | CODE | VAR NAME | NXT LVL VAR. | IMPCTD CATGY |
| | | | XYZ.txt | 1 | 11 | C MOVE L DATA APP#L2 | DATA | APP#L | TECH |
| | | | XYZ.txt | 1 | 85 | C MOVE DATA @ACODE2 | DATA | @ACODE | TECH |
| | | | XYZ.txt | 1 | 89 | CALL DATA WIND02 | DATA | | TECH |
| | | | YZX.txt | 2 | 103 | C PARM @APPLCOD | @APPL | | TECH |
| | | | ZXY.txt | 2 | 92 | C MOVE @ACODES9APPL | @ACODE | APPLCD | TECH |
| | | | ZXY.txt | 2 | 115 | C MOVE S9APPL @APPL2 | @APPL | | TECH |
| | | | BBT.txt | 3 | 47 | I12 APPLCD | APPLCD | | TECH |
| | | | BBT.txt | 3 | 54 | KFLD APPLCD | APPLCD | | TECH |

DETAIL | SUMMARY | CROSSREF | MISSING COMP | INSTR

FIG. 7

| | A | B | C | D |
|---|---|---|---|---|
| | COMPONENT NAME | COMPONENT TYPE | ICD-9 CODE | ICD-10 CODES |
| | C:\DOCUMENTS\ICD9_LIST | P.E.A.Reports.dll | 433.11 | |
| | C:\DOCUMENTS\ICD9_LIST | P.E.A.Reports.dll | 433.11 | |
| | C:\DOCUMENTS\ICD9_LIST | P.E.A.Reports.dll | 001.9 | |
| | C:\DOCUMENTS\ICD9_LIST | P.E.A.Reports.dll | 001.9 | |
| | C:\DOCUMENTS\ICD9_LIST | P.E.A.Reports.dll | 433.11 | |
| | C:\DOCUMENTS\ICD9_LIST | P.E.A.Reports.dll | 969.6 | |
| | C:\DOCUMENTS\ICD9_LIST | P.E.A.Reports.dll | 433.11 | |
| | C:\DOCUMENTS\ICD9_LIST | P.E.A.Reports.dll | 001.9 | |

FIG. 9

```
public class ClaimErrHandler : IVBSAXErrorHandler
{
    public ClaimErrHandler ()
    {
    }
    void IVBSAXErrorHandler.error(MSXML2.IVBSAXLocator ICtr, ref string strMsg, int ErrCode)
    {
/********START****SYNTEL****ICD10 CHANGES**********/
//      if (code=="433.11")
//      {
//          while (code=="433.11")
//          {
//          }
//      }
/*FOR ICD 10 condition*/
        if (code=="433.11")
        {
            while (code=="433.11")
            {
            }
        }
/********END****SYNTEL****ICD10 CHANGES*********/
```

FIG. 16

```
]Partial Class _Default
    Inherits System.Web.UI.Page

]   Protected Sub Button1_Click(ByVal sender As Object, ByVal e As System.EventArgs)
]   Handles Button1.Click '//****STARTSYNTELICD10 CHANGES*********/
'       While (code    = "001.9")
'       ,
'       End While
'//For ICD 9 condition
        While (code = "001.9")

End While
'//For ICD -10 condition
        While (code = 'A001.9")

End While
'//******END****SYNTEL****ICD10 CHANGES***********/

-   End Sub
-End Class
```

FIG. 17

```
'//**** SYNTEL ****ICD10****BELOW LINE IS IMPACTED**********/
    Dim a As Integer
'//*******START ****SYNTEL ****ICD10 CHANGES    **********/
    While (Code = 0001.9")
    .
    .
    .
        While (code = "001.9")
            'DATA MOVEMENT
            a = a + 1
            While (code = "001.9")
    .
    .
    .
                'OTHERS
                methodcall()
    .
    .
    .
            End While
        End While
'//For ICD 9 condition
        While (code = "001.9")
            'DATA MOVEMENT
            a = a + 1
            While (code = "001.9")
                'Others
                methodcall()
            End While
        End While
    End While
```

FIG. 18

```
(
------ SYNTEL ----- ICD -10 CHANGES  ----------  BELOW LINE IS IMPACTED   ---
 ---  @CodeType   varchar (5),
    @CodeType   varchar (8),
    @MapType   varchar (50),
    @Mode   int ,
    @Version  varchar (8)
)
```

FIG. 19

SYSTEM AND METHOD FOR AUTOMATICALLY MODIFYING SOURCE CODE TO ACCOMMODATE A SOFTWARE MIGRATION

CROSS-REFERENCE TO RELATED APPLICATION

This application claims the benefit of, and priority to, U.S. patent application Ser. No. 61/834,908, filed Jun. 14, 2013, the disclosure of which is incorporated herein by reference in its entirety.

FIELD OF THE INVENTION

This disclosure relates generally to a computerized system and method for healthcare-related data, and more specifically to a system and method for automatically modifying source code to accommodate a software migration such as from ICD-9 to ICD-10 code sets.

BACKGROUND

Healthcare legislation specifies procedures for communicating information within the healthcare industry. For example, Title II (Administrative Simplification provisions) of the Health Insurance Portability and Accountability Act of 1996 ("HIPAA") required the Department of Health and Human Services to establish national standards for electronic health care transactions and national identifiers for providers, health plans, and employers.

On Jan. 1, 2012, an updated version of the healthcare transactions standard, HIPAA 5010, replaced version 4010A1, the current set of standards. Among various changes in this update, HIPAA 5010 mandates changes to the International Classification of Diseases ("ICD"), which is a nomenclature for the classification of diseases, injuries, and other medical conditions. More specifically, HIPAA 5010 requires healthcare payers and providers to transition from the current International Classification of Diseases, 9th Revision, Clinical Modification ("ICD-9") to a 10th revision ("ICD-10"). This transition is referred to herein as the "ICD-10 migration" and, at present, all healthcare stakeholders (e.g., providers, payers, and employers), must make this transition by Oct. 1, 2015.

ICD-10 codes exhibit fundamental differences as compared with ICD-9 codes. For example, the form and information conveyed in ICD-10 codes is different than that of the ICD-9 codes. More specifically, ICD-9 codes contain three to five digits beginning with either a number or a letter, with a decimal point placed after the third digit, and the ICD-9 book indicates the level of specificity for each code. ICD-10 codes, on the other hand, are seven digits in length. The first three digits of the ICD-10 codes are similar to the ICD-9 codes, with a decimal point after the third digit. However, the digits that follow the decimal point have different, specific meanings. For medical and surgical procedures, for example, the digits that follow are specific to body part, surgical approach, and other qualifiers needed for billing. Similarly, the ICD-10 codes that represent diagnosis codes also have seven digits.

The first three digits of ICD-10 codes are similar to the ICD-9 code, but the additional digits add specificity to the code such as laterality, chronic versus acute, and so on. Another significant difference between the ICD-9 and ICD-10 code sets is the number of codes. More specifically, ICD-9 includes just over 14,000 diagnosis codes and almost 4,000 procedural codes. In contrast, ICD-10 contains over 68,000 diagnosis codes (clinical modification codes) and over 72,000 procedural codes. Due to such fundamental differences, mapping or translation from the ICD-9 code set to the ICD-10 code set presents challenges to ICD-10 migration. For example, while there are some one-to-one correspondences between ICD-9 and ICD-10 codes, there are also one-to-many, many-to-one and many-to-many correspondences and, in some cases, no correspondence at all. Accordingly, ICD-10 migration will undoubtedly affect many aspects of information collection, reporting requirements, billing and payment systems, potentially resulting in benefit, financial and clinical variations.

SUMMARY

The present invention may comprise one or more of the features recited in the attached claims, and/or one or more of the following features and combinations thereof. In one aspect, a system for automatically modifying source code to accommodate a software migration, the system comprises a data management module to selectively receive a software codebase that supports international classification of diseases, ninth revision (ICD-9) codes and that contains a plurality of lines of source code, to selectively receive a codebase impact assessment report identifying each impacted line of the plurality of lines of source code in the codebase, each impacted line requiring modification in order to support migration from ICD-9 codes to international classification of diseases, tenth revision (ICD-10) codes, and a codebase modification module responsive to activation thereof to automatically modify the codebase by modifying each impacted line of source code identified in the codebase impact assessment report so that the modified codebase supports migration from ICD-9 codes to ICD-10 codes.

In another aspect, a computerized method for automatically modifying source code to accommodate a software migration comprises receiving by a processor a software codebase a software codebase that supports international classification of diseases, ninth revision (ICD-9) codes and that contains a plurality of lines of source code, receiving by the processor a codebase impact assessment report identifying each impacted line of the plurality of lines of source code in the codebase, each impacted line requiring modification in order to support migration from ICD-9 codes to international classification of diseases, tenth revision (ICD-10) codes, and in response to a user input, automatically modifying the codebase with the processor by modifying each impacted line of source code identified in the codebase impact assessment report so that the modified codebase supports migration from ICD-9 codes to ICD-10 codes.

In still another aspect, a computer program product comprises a non-transitory computer readable medium having instructions stored thereon which, when executed by at least one processor, causes the processor to receive a software codebase a software codebase that supports international classification of diseases, ninth revision (ICD-9) codes and that contains a plurality of lines of source code, receive a codebase impact assessment report identifying each impacted line of the plurality of lines of source code in the codebase, each impacted line requiring modification in order to support migration from ICD-9 codes to international classification of diseases, tenth revision (ICD-10) codes, and in response to a user input, automatically modify the codebase by modifying each impacted line of source code identified in the codebase impact assessment report so that the modified codebase supports migration from ICD-9 codes to ICD-10 codes.

BRIEF DESCRIPTION OF THE DRAWINGS

This disclosure is illustrated by way of example and not by way of limitation in the accompanying FIGS. Where considered appropriate, reference labels have been repeated among the FIGS. to indicate corresponding or analogous elements.

FIG. 7 is an example of a codebase impact assessment report of the type selected in FIG. 6.

FIG. 9 is an example of a code set mapping report of the type selected in FIG. 6.

FIG. 16 is an example of a modification made by the source code modification tool to one line of source code in a codebase such that the modified codebase will thereafter support a single code set.

FIG. 17 is an example of a modification made by the source code modification tool to source code in a codebase such that the modified code base will thereafter support multiple code sets.

FIG. 18 is an example modification made by the source code modification tool to source code in a codebase to include data declaration and data movement.

FIG. 19 is an example modification made by the source code modification tool to source code in a codebase to modify data field length.

DETAILED DESCRIPTION OF THE DRAWINGS

Figure 1:
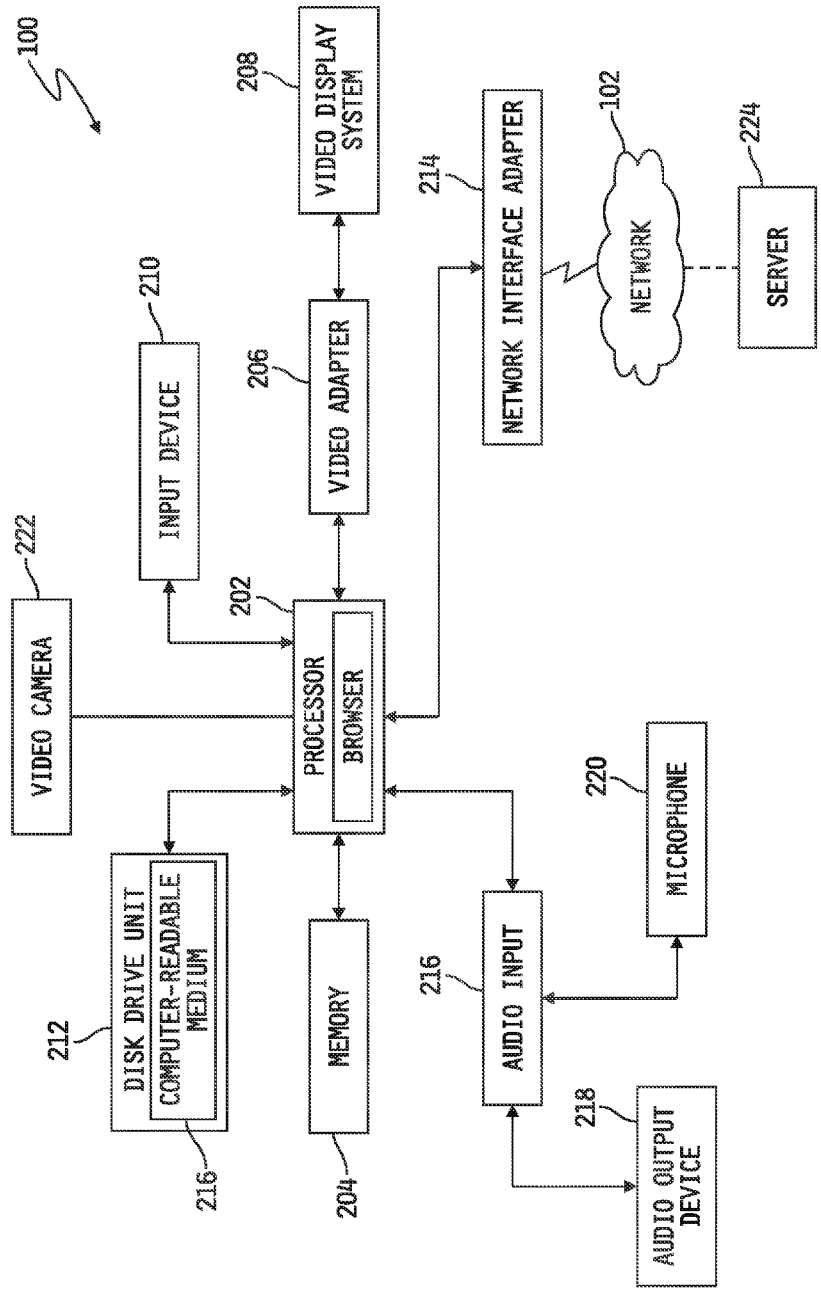
FIG. 1 is a simplified block diagram of an embodiment of a computerized system that may be programmed with a set of instructions to perform any one or more of the functions, processes and methods discussed herein.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

This application relates to the following applications all filed on even date herewith, the disclosures of which are incorporated herein by reference in their entirety; U.S. patent application Ser. No. 14/306,060, entitled System and Method for Providing Mapping Between Different Disease Classification Codes U.S. patent application Ser. No. 14/306,208, entitled System and Method for Ensuring Medical Benefit Claim Payment Neutrality Between Different Disease Classification Codes, U.S. patent application Ser. No. 14/305,994, entitled System and Method for Analyzing an Impact of a Software Code Migration, and U.S. patent application Ser. No. 14/306,077, entitled System and Method for Validating Medical Claim Data.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases may or may not necessarily refer to the same embodiment. Further, when a particular feature, structure, process, process step or characteristic is described in connection with an embodiment, it is submitted that it is within the knowledge of one skilled in the art to effect such feature, structure, process, process step or characteristic in connection with other embodiments whether or not explicitly described. Further still, it is contemplated that any single feature, structure, process, process step or characteristic disclosed herein may be combined with any one or more other disclosed feature, structure, process, process step or characteristic, whether or not explicitly described, and that no limitations on the types and/or number of such combinations should therefore be inferred.

Embodiments of this disclosure may be implemented in hardware, firmware, software, or any combination thereof. Embodiments of this disclosure implemented in a computer system may include one or more bus-based interconnects between components and/or one or more point-to-point interconnects between components. Embodiments of this disclosure may also be implemented as instructions stored on one or more machine-readable media, which may be read and executed by one or more processors. A machine-readable medium may be embodied as any device or physical structure for storing or transmitting information in a form readable by a machine (e.g., a computing device). For example, a machine-readable medium may be embodied as any one or combination of read only memory (ROM); random access memory (RAM); magnetic disk storage media; optical storage media; flash memory devices; and others.

Referring now to FIG. 1, an embodiment is shown of a system 100 for modifying source code to accommodate a software code migration, e.g., from an ICD-9 code set to an ICD-10 code set. Although a migration from ICD-9 to ICD-10 is discussed herein for purposes of example, this disclosure is not intended to be limited to migration from ICD-9 to ICD-10, but encompasses migration from any one medical classification system to another medical classification system. The computing device 100 may be a personal computer, a tablet computer, a personal digital assistant ("FDA"), a media player, a cellular telephone, or any machine capable of executing a set of instructions (sequential or otherwise) that specify actions to be taken. The system 100 according to embodiments of the present disclosure may include a processor 202 (e.g., a central processing unit ("CPU")), a memory 204, a video adapter 206 that drives a video display system 208 (e.g., a liquid crystal display ("LCD"), a cathode ray tube ("CRT"), a touch screen), an input device 210 (e.g., a keyboard, mouse, touch screen display, etc.) for the user to interact with the program (e.g., browser), a disk drive unit 212, a network interface adapter 214, an audio in/out jack 216 that allows audio to be outputted/received by an audio output device 218 (e.g., speaker, headphones) and microphone 220, respectively. Although a combined audio in/out jack 216 is shown for purposes of example, one skilled in the art should appreciate that separate devices may be provided for input and output of audio. It will be understood that that various embodiments of the computing device 100 may not always include all of these peripheral devices, and may instead include various subsets thereof. It will further be understood that the video display system 208 may, in some embodiments, be provided in the form of one or more conventional display monitors.

The disk drive unit 212 includes a computer-readable medium 216 on which may be stored a program code for a web browser with commonly installed plugin(s), such as Flash™ and/or Java™. In some cases, the browser may provide support for the emerging HTML5 WebRTC standard. Embodiments are also contemplated in which the browser could be on a mobile internet connected device, such as a phone or tablet, which has support for the emerging HTML5 WebRTC standard. In one embodiment, a custom application could be provided on an Internet connected mobile device. The term "computer-readable medium" shall be taken to include, but not be limited to, solid-state memories, optical media, flash memory, and magnetic media. Embodiments are contemplated in which the browser may run applications that are received from a server 224 over a network 102 via the network interface device 214 utilizing any one of a number of transfer protocols including but not limited to the hypertext transfer protocol ("HTTP") and file transfer protocol ("FTP"). The network 102 may be any type of packet-switched data network including but not limited to fiber optic, wired, and/or wireless communication capability in any of a plurality of protocols, such as TCP/IP, Ethernet, WAP, IEEE 802.11, or any other protocol.

Compliance with the above discussed migration from the ICD-9 code set to the ICD-10 code set is expected to impact the software and systems of health care providers and payers. Embodiments of the present disclosure are directed to a source code modification tool which automatically modifies lines of source code that are impacted by the ICD-9 to ICD-10 migration. Such software source code used in current health care systems may be generically referred to herein as a "codebase," and the term "source code" may therefore at times be replaced in the following description with "codebase," e.g., the following description may refer to "codebase modification tool," "codebase modification module" and the like, and it will be understood that in such contexts, "codebase" means a collection of software source code such as may be used in and with health care systems.

In order to accomplish such source code or codebase modifications, the source code modification tool described herein makes use of a codebase impact assessment report which identifies each impacted line of source code of a codebase, i.e., each line of source code that is impacted by the ICD-9 to ICD-10 migration. As used herein, the term "impacted line" in the context of a line of source code that is "impacted by" the ICD-9 to ICD-10 migration, is defined as a line of source code in a codebase that requires modification in order to support the ICD-9 to ICD-10 migration. Examples of modifications that may be made to an "impacted line" of source code in order for the modified codebase to support the ICD-9 to ICD-10 migration include, but are not limited to, (1) modifying an ICD-9 code with a mapping to at least one corresponding ICD-10 code, (2) modifying at least one data field length, (3) adding at least one data field, (4) renaming at least one data field, (5) modifying at least one data type, (6) modifying at least one logical expression in the line of source code, (7) adding at least one data declaration, and (8) adding at least one data movement instruction. In any case, such a codebase impact assessment report may illustratively be imported into the source code modification tool or created within the tool. One example of a codebase impact assessment report suitable for use by the source code modification tool described herein, and which may therefore be imported into the tool, is illustrated and described in co-pending U.S. patent application Ser. No. 14/305,994, entitled System and Method for Analyzing an Impact of a Software Code Migration, which has been incorporated herein by reference in its entirety. Alternatively or additionally, a codebase impact assessment report may be created by the source code modification tool using a downloadable template as will he described in greater detail below.

The source code modification tool described herein further makes use of an ICD-9 to ICD-10 mapping in order to modify impacted lines of source code in the selected codebase that contain one or more ICD-9 codes to thereafter support one or more corresponding ICD-10 codes. In this regard, the source code modification tool may be selectively configured to modify the impacted lines of source code such that the modified codebase will support only the ICD-10 code set, or to modify the impacted lines of source code such that the modified codebase will support both of the ICD-9 and the ICD-10 code sets. In either case, the ICD-9 to ICD-10 mapping may illustratively be imported into the source code modification tool or created based on the subset of the ICD-9 code set contained in the selected codebase. One example process for determining such a subset of the ICD-9 code set contained within a selected codebase, and which may be imported into the tool for subsequent completion of the ICD-9 to ICD-10 mapping, is illustrated and described in co-pending U.S. patent application Ser. No. 14/305,994, entitled System and Method for Analyzing an Impact of a Software Code Migration. An example process for completing the ICD-9 to ICD-10 mapping or migration, using the subset of the ICD-9 code set contained within the selected codebase, is illustrated and described in co-pending U.S. patent application Ser. No. 14/306,060, entitled System and Method for Providing Mapping Between Different Disease Classification Codes, which has been incorporated herein by reference in its entirety.

The source code modification tool described is configured to, and is operable to, modify impacted lines of source code in a selected code base by any one or more of (1) modifying an ICD-9 code contained in an impacted line of the source code with a mapping to at least one corresponding ICD-10 code, (2) modifying at least one data field length, (3) adding at least one data field, (4) renaming at least one data field, (5) modifying at least one data type, (6) modifying at least one logical expression in the impacted line of source code, (7) adding at least one data declaration, and (8) adding at least one data movement instruction. Alternatively or additionally, the source code modification tool may modify the source code in the selected codebase by inserting comments before and/or after each impacted line of source code in the selected codebase that is modified by the source code modification tool. These and other features of the source code modification tool are described in detail below.

Figure 2:
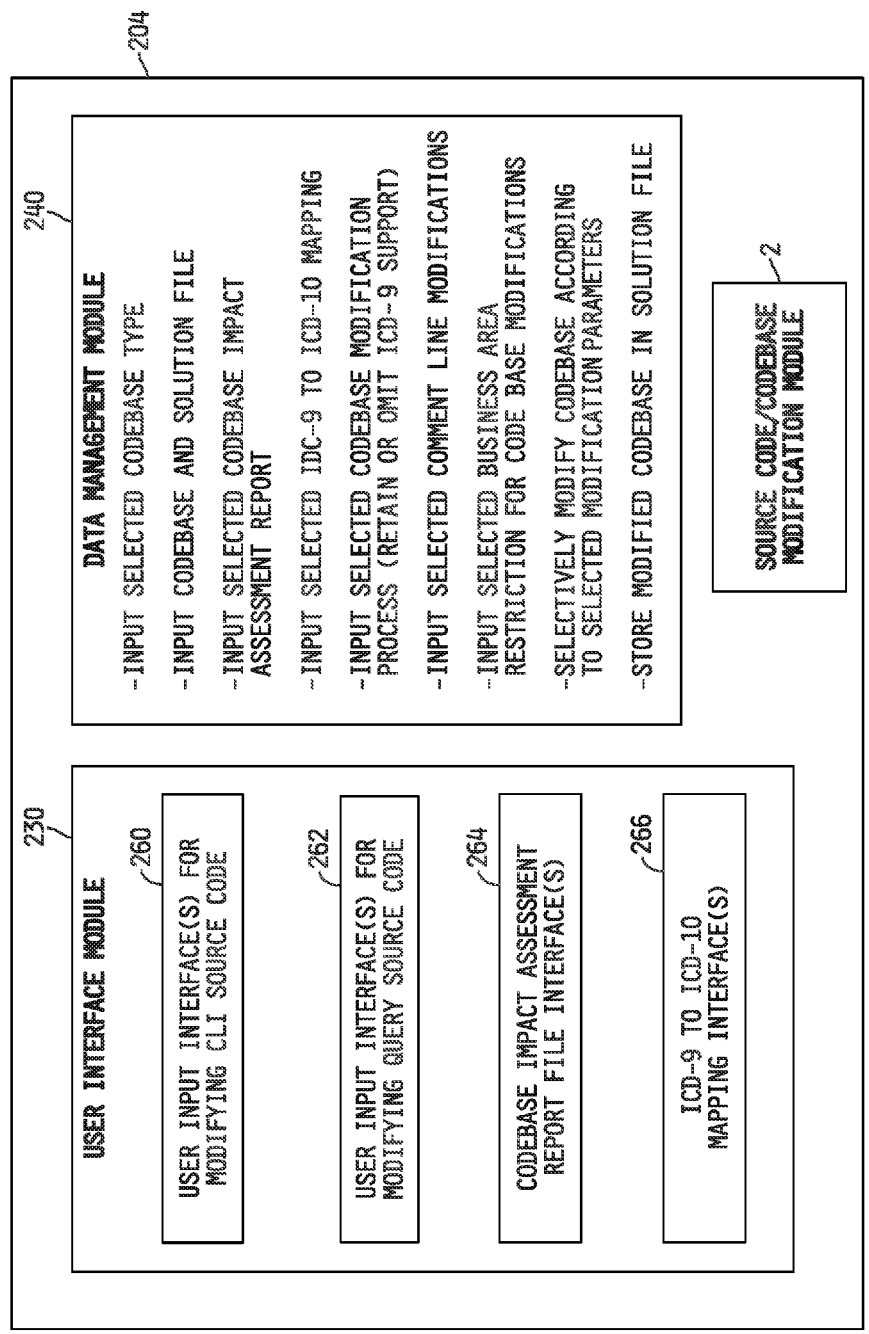
FIG. 2 is a simplified block diagram representation of a source code modification tool executed by the system illustrated in FIG. 1.

Referring now to FIG. 2, a simplified block diagram is shown of a software environment of the system of FIG. 1. In the illustrated embodiment, the source code modification tool is implemented in the form of instructions stored in the memory 204 of the system 100 and executable by the processor 202 to perform the functions described herein. Alternatively or additionally, the instructions may be stored in whole or in part on the computer-readable medium 216, and/or on the server 224 and accessed by the processor 202 via the network 102. Alternatively or additionally still, the server 224 may include one or more processors which execute the instructions, and input/output data may be exchanged between the processor 202 and the server 224 via the network 102. In any case, the source code modification tool includes a user interface module 230, a data management module 240, and a source code/codebase modification module 250 (which may be referred to interchangeably hereinafter as "source code modification module" or "codebase modification module").

The user interface module 230 includes a number of graphic user interfaces for receiving user inputs and user selections of reports/files for configuring the source code modification tool for operation. In the illustrated embodiment, for example, the user interface module 230 includes user interfaces for configuring the source code modification tool to modify source code written in various computer programming languages. In one embodiment, the source code modification tool supports common language infrastructure (CLI) programming languages such as, but not limited to, C# and VB.NET (and some similar programming languages such as, but not limited to Java), as well as query-based programming languages, such as, but not limited to, structured query language (SQL) script, Oracle Script and the like. In this regard, the user interface module 230 illustratively includes one or more user input interfaces 260 for receiving user input for configuring the source code modification tool to modify CLI source code, and one or more user input interfaces 262 for receiving user input for configuring the source code modification tool to modify query-based source code. Those skilled in the art will recognize that the source code modification tool may alternatively be configured to modify source code of codebases written in other computer programming languages, and that such alternate configurations of the source code modification tool described herein will be a mechanical step for a skilled programmer. As such, it will be understood that any such alternate configuration of the source code modification tool to accommodate and operate on source code written in a computer programming language other than a CLI or query-based language is intended to fall within the scope of this disclosure.

The user interface module illustratively further includes one or more user interfaces 264 for selecting, inputting (i.e., importing) and/or constructing codebase impact assessment reports, and one or more user interfaces 266 for selecting, inputting (i.e., importing) and/or constructing ICD-9 to ICD-10 mappings (i.e., map file(s)). It will be understood that while some embodiments may include all such interfaces 260-266, other embodiments may include various subsets of such interfaces. Examples of some such graphic user interfaces are illustrated in one or more of FIGS. 4-15 attached hereto.

The data management module 240 manages the input of information to, and user control of, the source code modification tool. For example, the data management module 240 illustratively manages the selection and input to the tool of a codebase type selected by the user, of the selection an input to the tool of a codebase and solution file, of the selection and input (and/or construction) of codebase impact assessment reports, of the selection and input (and/or construction) of one or more ICD-9 to ICD-10 mappings, of the selection and input of a desired codebase modification process (i.e., to omit or retain ICD-9 support by the resulting modified codebase), of the selection and input of comment line modifications, and of the selection and input of a business area restriction for codebase modifications. The data management module 240 further illustratively manages the exportation and storage of the codebase modifications (i.e., lines of source code modified by the source code modification tool) in a selected solution file of an electronic data storage medium (e.g., memory 204, computer-readable medium 216, server 224 and/or other electronic data storage medium.

The source code/codebase modification module 250 (which may at times be referred to herein as a "source code modification module" or a "codebase modification module") illustratively operates to automatically modify impacted lines of source code contained in a selected codebase in accordance with configuration settings of the source code modification tool that are selected by the user. Examples of some such source code modifications are illustrated in FIGS. 16-19 attached hereto.

Figure 3:
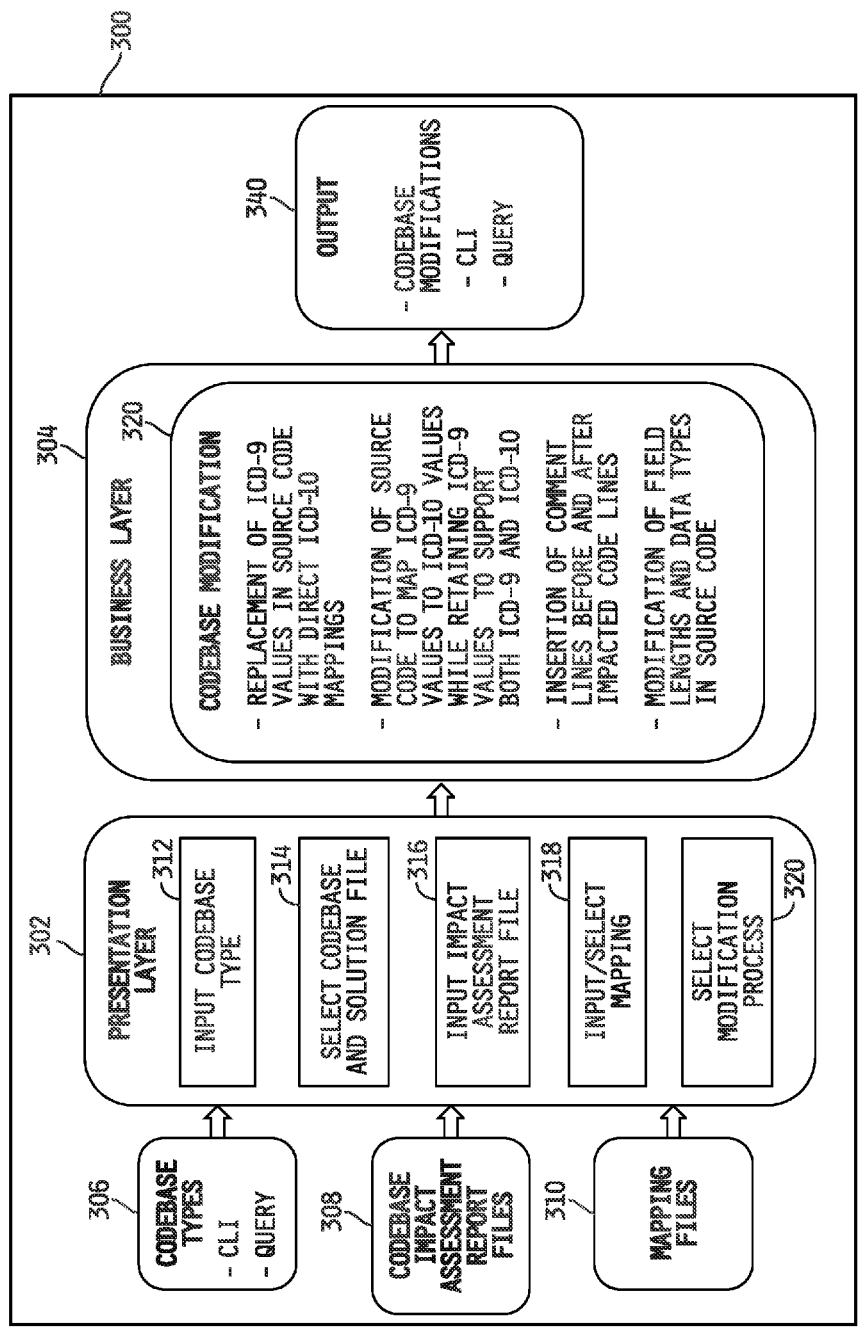
FIG. 3 is a simplified block diagram depicting an example architecture of the software code modification tool.

FIG. 3 is a block diagram illustrating an example architecture 300 of the software code modification tool. The architecture 300 includes, but is not limited to, a presentation layer 302 and a business layer 304. The presentation layer 302 illustratively provides an interface 312 for the user to select and input one or more codebase types 306; i.e., of the type of computer programming language of the source code in the selected codebase of a healthcare system software application that supports at least the ICD-9 code set. The tool illustratively supports modification of source code or codebases provided in various different programming languages, examples of which include, but are not limited to, C#, VB, .NET, SQL Script, Oracle Script, Java, etc. The presentation layer 302 further illustratively provides an interface 314 for the user to select a codebase to modify and a corresponding codebase solution file (e.g., in which to store the modified codebase and/or modifications to the selected codebase), an interface 316 for the user to select and input one or more impact assessment report files 308, an interface 318 for the user to select and input one or more ICD-9 to ICD-10 mappings files 310, and an interface 320 for the user to selectively activate the source code modification process (in accordance with the user-selected files and configuration/parameter settings).

The business layer 304 contains the components which implement the business logic and rules responsible for the functionality of the source code modification tool. For example, a codebase modification component 330 illustratively includes, but is not limited to, the functionality of selectively replacing ICD-9 code values in one or more impacted lines of source code with selected, direct ICD-10 mappings, alternatively selectively modifying one or more impacted lines of source code to map ICD-9 code values to one or more corresponding ICD-10 code values while also retaining the ICD-9 code values to support both ICD-9 and ICD-10 code sets, modifying at least one data field length in one or more impacted lines of source code, adding at least one data field in one or more impacted lines of source code, renaming at least one data field in one or more impacted lines of source code, modifying at least one data type in one or more impacted lines of source code, modifying at least one logical expression in one or more impacted lines of source code, adding at least one data declaration in one or more impacted lines of source code, adding at least one data movement instruction in one or more impacted lines of source code, and/or inserting comment lines before and/or after one or more impacted lines of source code.

The output 340 of the business layer 304 is a modified codebase, i.e., as modified according to the source code modification process described herein, which is illustratively stored in an electronic data storage medium in a solution file selected by the user.

Figure 4:
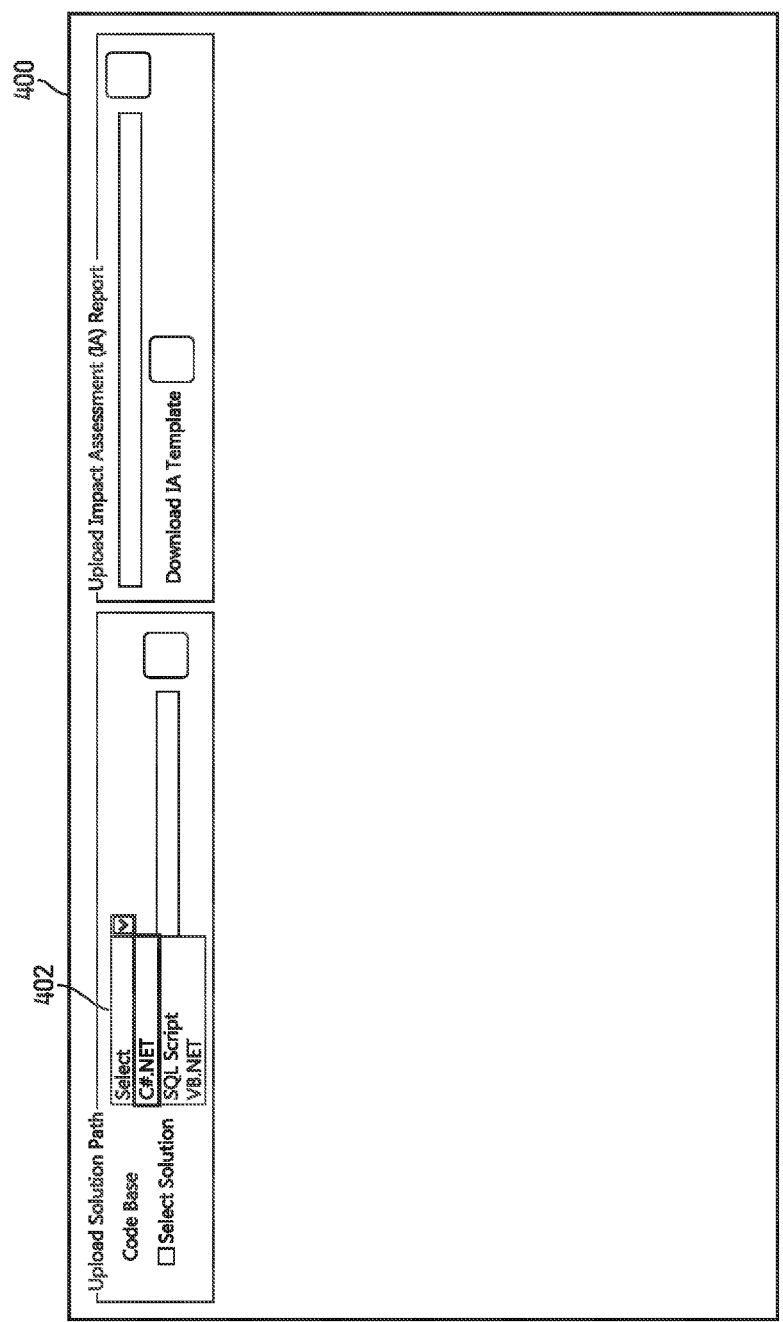
FIG. 4 is an example screen shot illustrating a process for selecting a codebase of one type for processing by the source code modification tool illustrated in FIGS. 2 and 3.
Figure 5:
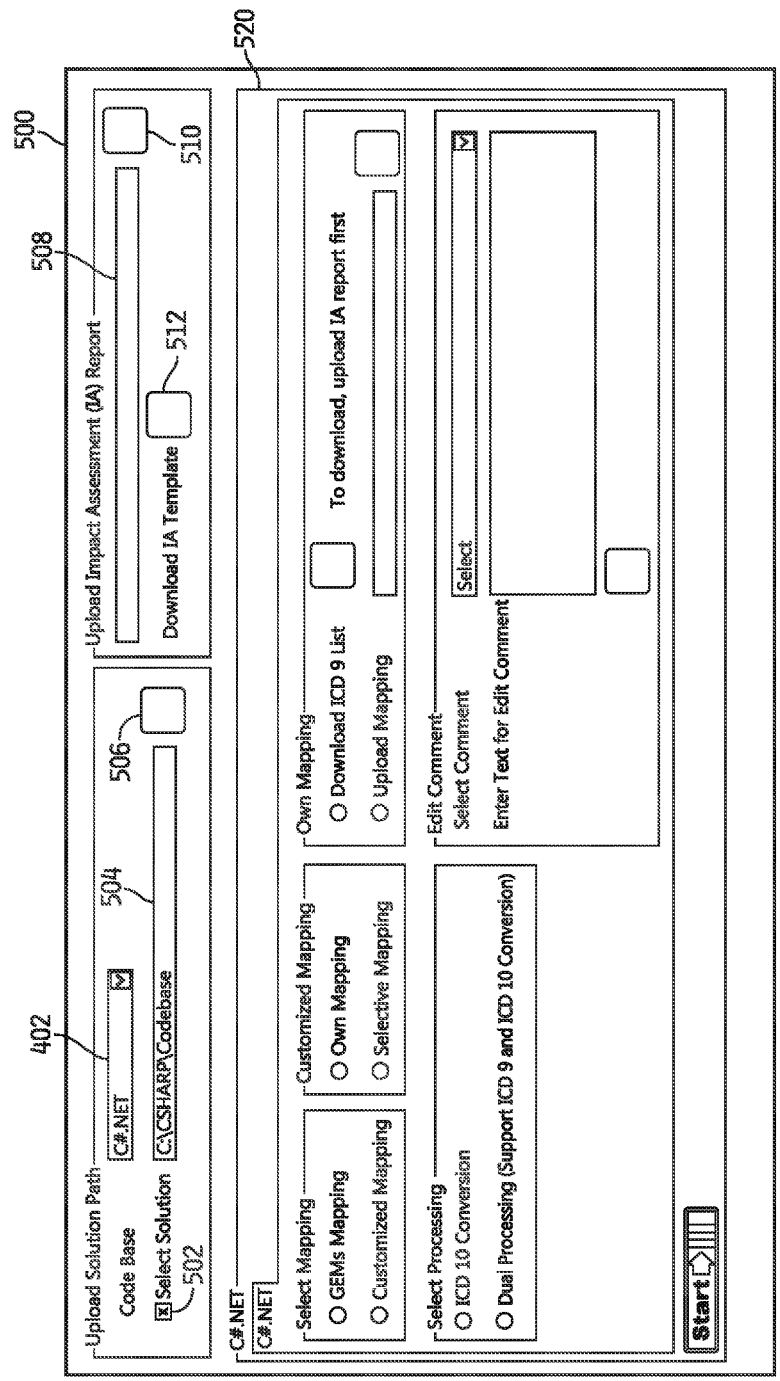
FIG. 5 is an example of a screen shot illustrating a process for selecting a destination file for the selected codebase that will be modified by the source code modification tool illustrated in FIGS. 2 and 3.

Upon loading the tool, as shown in FIG. 4, a user is presented with a main menu screen 400, which illustratively includes a codebase type input 402, e.g., in the form of a pull-down menu of codebase types (i.e., the codebase types correspond to the computer programming language in which the source code of the codebase is written). In the screen shot of FIG. 4, the available codebase types include C#.NET, SQL Script and VB.NET, and the user has selected C#.NET as the type of codebase file that will be subsequently identified and input to the tool. With the codebase type selected, the screen shot 500 of FIG. 5 illustrates a tool interface with various components or parameters of the tool that require input and/or selection by the user, some of which are specific to the type of codebase selected, e.g., a user interface 520. In the screen shot of FIG. 5, C#.NET is the selected codebase type.

Referring to FIG. 5, a screen shot 500 illustrates a codebase solution input graphic 502 which, if selected by the user, allows the user to enter into an input interface 504 a file path identifying a location in an electronic data storage medium in which the codebase to be modified is stored and where the modifications to the selected codebase (i.e., the modified lines of source code of the selected codebase), as modified by the source code modification tool, and/or a modified version of the selected codebase, will be stored. Illustratively, the modified file path interface 504 may include a file browsing button 506 which the user may activate to browse, i.e., search for, a specific file path. If the user does not select the codebase solution input graphic 502, the tool illustratively selects a default file path at which to retrieve a codebase for modification and at which to store the codebase modifications. In one embodiment, the default destination path is the library name of the codebase identified in the impact analysis (IA) report described below, although alternative embodiments are contemplated in which the default destination path may be or include one or more other storage locations.

Figure 6:
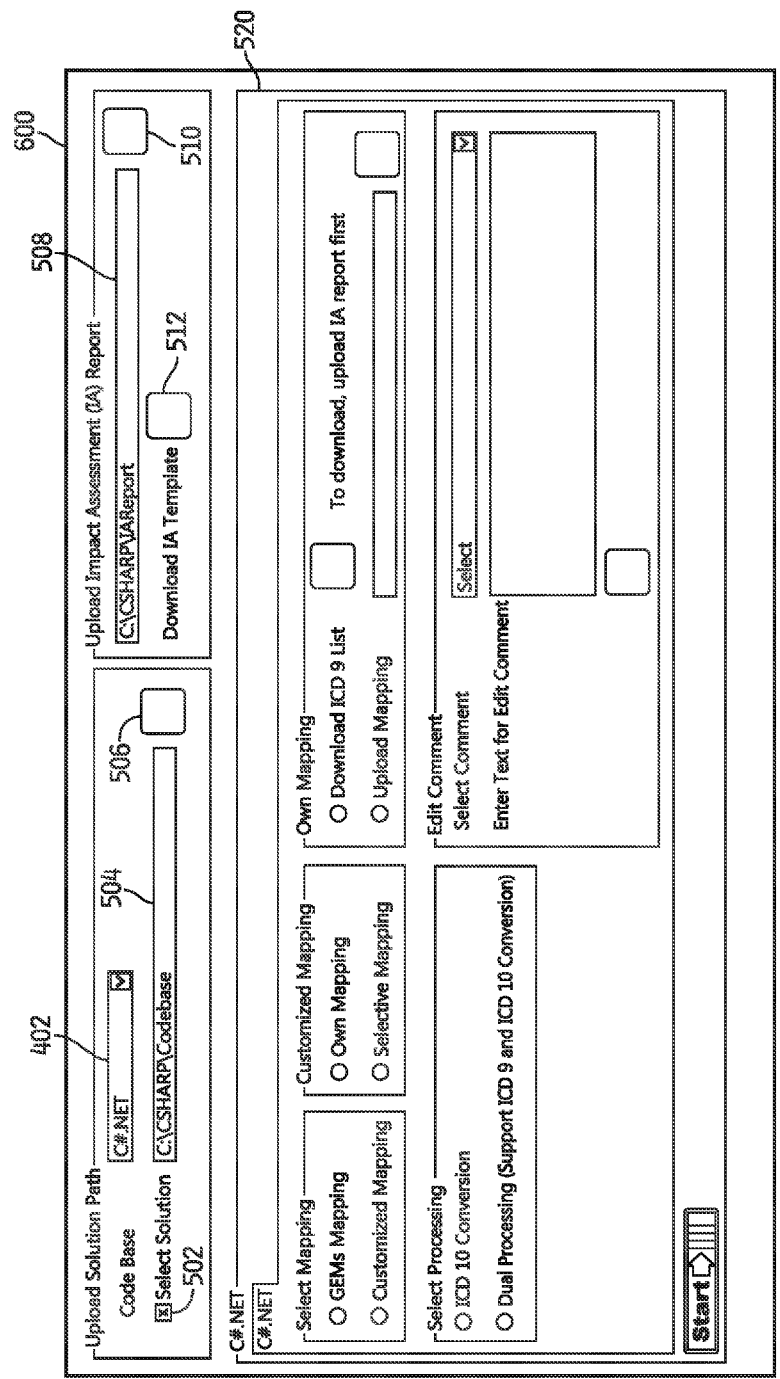
FIG. 6 is an example of a screen shot illustrating a process for selecting or creating a codebase impact assessment report for use by the source code modification tool in modifying the selected codebase.

Referring now to FIG. 6, a screen shot 600 is shown which represents the state of the tool interface after selection of the codebase type and codebase/solution file path. The tool interface illustrated in FIG. 6 includes a codebase impact analysis report input interface 508 via which the user may specify a codebase impact assessment (IA) report to upload (i.e., input) to the data management module 240. Illustratively, the IA report interface 508 may include a file browsing button 510 which the user may activate to browse, i.e., search for, a specific IA report stored in a memory location. The codebase impact analysis report illustratively identifies each of the ICD-9 codes contained in a selected codebase, which may comprise a subset of the entire ICD-9 code set or which may include the entire ICD-9 code set.

The codebase impact analysis report further illustratively identifies each impacted line of a plurality of lines of source code making up the codebase. One or more impacted lines of source code may illustratively include only a single ICD-9 code, and in such cases the codebase impact analysis report illustratively identifies each of the plurality of lines of source code in the codebase that contains an ICD-9 code. This disclosure contemplates other embodiments in which one or more lines of source code may include more than one ICD-9 code, and in such embodiments the codebase impact analysis report illustratively identifies each of the plurality of lines of source code in the codebase that contains at least one ICD-9 code.

One example of a codebase impact assessment report suitable for use by the source code modification tool described herein, and which may therefore be imported into the tool, is illustrated and described in co-pending U.S. patent application Ser. No. 14/305,994, entitled System and Method for Analyzing an Impact of a Software Code Migration, an example 700 of which is shown in FIG. 7 in Excel™ report format. The illustrated IA report 700 includes a number of different report types for a selected codebase, and each report type is available via a different tab in the application. For example, the IA report 700 illustratively includes a detail report, as illustrated in FIG. 7, a summary report, a cross-reference report and a missing component report. The detail report shown in FIG. 7 illustratively includes, e.g., arranged by columns, library name, component name, component type, file name, iteration number, line number, code, variable name next level variable and impacted category. Each line of source code identified (e.g., by line number) in the detail IA report 700 shown in FIG. 7 is an impacted line of source code, and the detail IA report 700 thus comprises an identification, e.g., in the form of a detailed list, of each of the plurality of lines of source code in the selected codebase that is an impacted line of source code.

Alternatively to selecting and inputting an IA report for a selected codebase (e.g., via the IA report interface 508), a codebase impact assessment report may be created within source code modification tool using a downloadable template available via user selection of a codebase impact analysis template download button 512 as illustrated in FIGS. 5 and 6. Illustratively, the IA template may be provided as an unpopulated version of the IA report illustrated in FIG. 7, although this disclosure contemplates that other suitable IA template forms may alternatively be used without departing from the scope of thereof.

Figure 8:
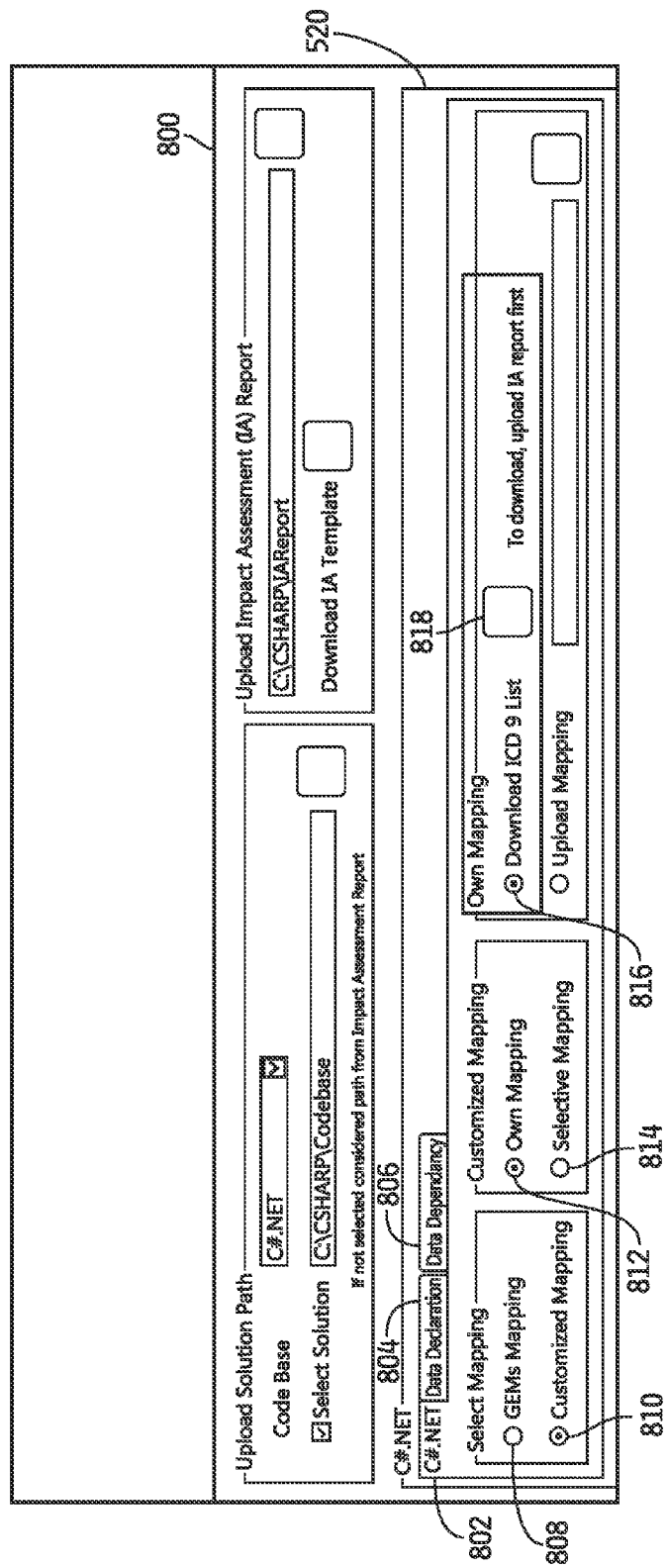
FIG. 8 is an example screen shot illustrating a process for selecting a code set mapping for use by the source code modification tool in modifying the selected codebase.
Figure 10:
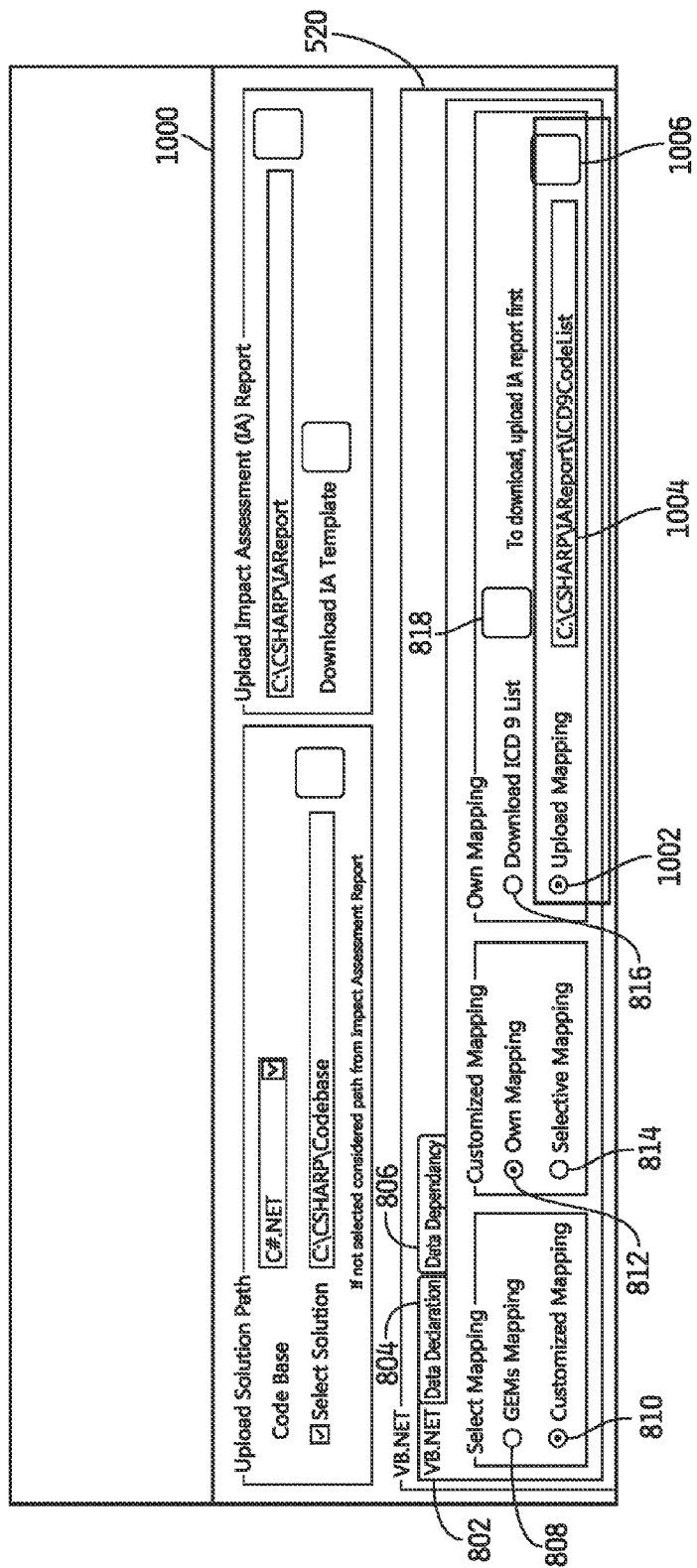
FIG. 10 is an example screen shot illustrating another process for selecting a code set mapping for use by the source code modification tool in modifying the selected codebase.

Referring now to FIG. 8, a screen shot 800 is shown which represents the state of the tool interface after selection of the codebase impact analysis report. As illustrated in FIG. 8, the user interface 520 includes a number of user-selectable tabs 802, 804 and 806, with the tab 802 being specifically illustrated in FIG. 8. The tab 802 of the user interface 520 includes features for identifying and inputting a mapping file, i.e., a map file containing a plurality of maps each of which map a different ICD-9 code to one or more corresponding ICD-10 codes. Regardless of the type or source of the map file, this disclosure contemplates at least two different types of map files, in terms of quantity of content that may be used by the source code modification tool. In embodiments in which the selected codebase includes only a subset of the entire ICD-9 code set, for example, the map file may include only those mappings that map the subset of ICD-9 codes to one or more corresponding ICD-10 codes. Alternatively, and in embodiments in which the selected codebase includes the entire ICD-9 code set, the map file may include all mappings between each of the ICD-9 codes in the entire ICD-9 code set and the one or more corresponding ICD-10 codes.

In any case, the user interface 520 provides for user selection of the map file in the form of a general equivalence mappings (GEMs) map file, via user selection of a radio button 808, or a customized mapping, via user selection of a radio button 810. User selection of the GEMs radio button 808 illustratively invokes a web service that provides for user selection of the map file(s) in the form of one or more GEMs files. User selection of the customized mapping radio button 810, on the other hand, allows the user to select or construct the map file(s) from the user's own mapping files by selection of an "own mapping" radio button 812. By selecting this option, the user may provide a customized map file by selecting the ""Download ICD 9 List" radio button 816. In so doing, the user will illustratively be instructed to first upload a list of the ICD-9 codes contained in the selected codebase. As illustrated in the screen shot of FIG. 10, the user may thus select an "Upload Mapping" radio button 1002 and then identify in a file input interface 1004, e.g., with or without the assistance of a browsing button 1006, a source path for the ICD 9 List. One example of such an ICD 9 List which is suitable for use by the source code modification tool described herein, is illustrated and described in co-pending U.S. patent application Ser. No. 14/305,994, entitled System and Method for Analyzing an Impact of a Software Code Migration. In alternative embodiments, the ICD 9 List may be obtained elsewhere or otherwise constructed from the selected codebase.

In any case, once obtained, the user can select an ICD 9 List download button 818 to download the ICD 9 List to an application that constructs or otherwise provides the ICD-9 to ICD-10 code mapping based on the ICD-9 codes in the ICD 9 List. An example of an ICD 9 List 900 that may be downloaded to an ICD-9 to ICD-10 mapping application is illustrated in FIG. 9 and includes a listing of all ICD-9 codes in the selected codebase by component name and component type.

An example of an application that may be used to construct an ICD-9 to ICD-10 mapping, e.g., from the ICD 9 List described above, is illustrated and described in co-pending U.S. patent application Ser. No. 14/306,060, entitled System and Method for Providing Mapping Between Different Disease Classification Codes. This disclosure contemplates that other applications or services may alternatively provide an ICD-9 to ICD-10 mapping for the selected code set without detracting from the scope thereof. In any case, the selected map file illustratively contains a plurality of mappings, each mapping a different ICD-9 code to one or more corresponding ICD-10 codes.

Figure 11:
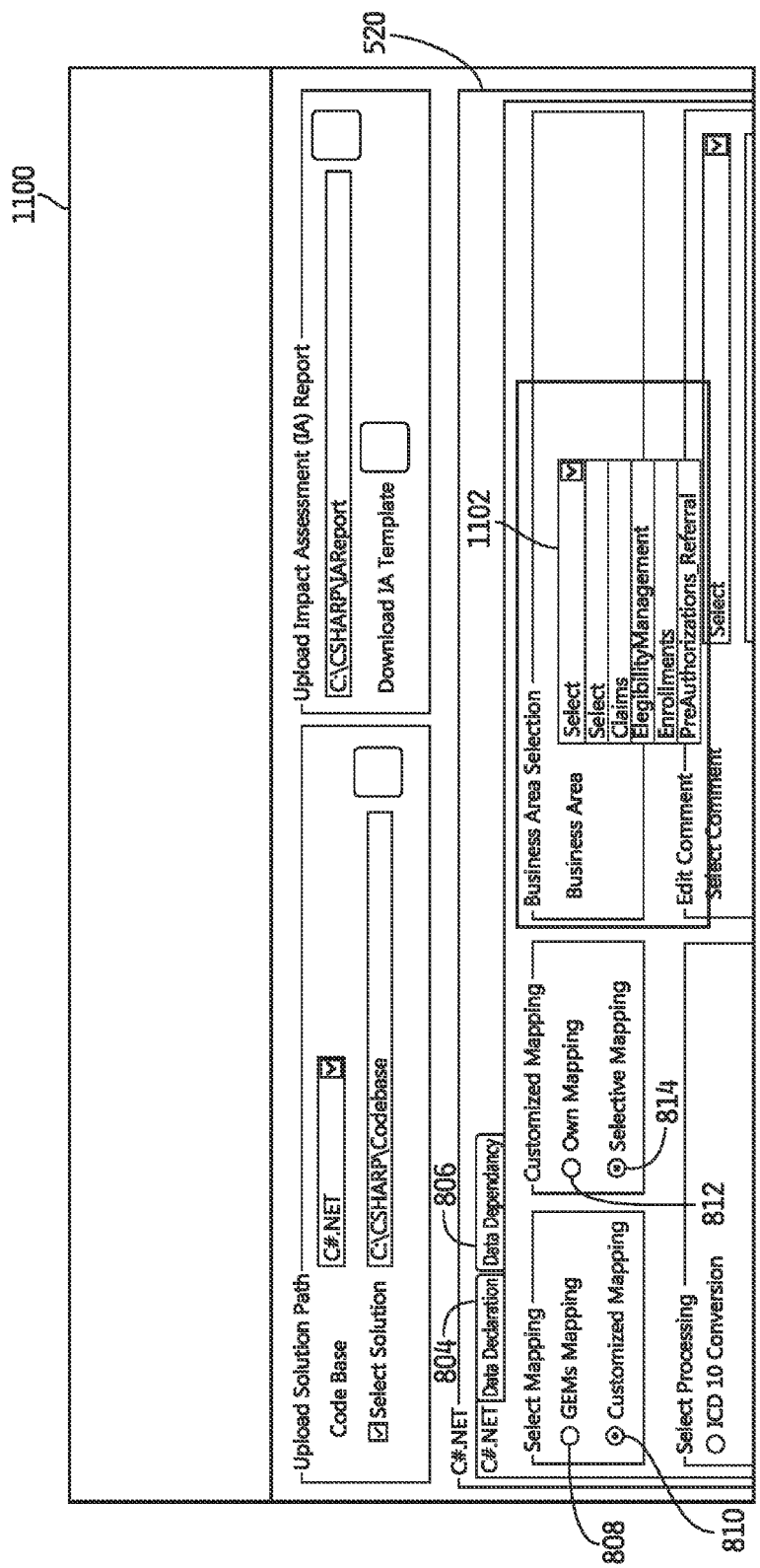
FIG. 11 is an example screen shot illustrating a process for selecting a business area to which code set mapping will be restricted by the source code modification tool in modifying the selected codebase.

Referring now to FIG. 11, the tab 802 of the user interface 520 in the illustrated screen shot 1100 includes another customized mapping option alternatively to or in addition to the user supplying one or more custom map files; namely, a selective mapping feature. By selecting the selective mapping radio button 814, the user interface 520 produces a business area selection interface 1102 via which the user can restrict the source code modifications made by the source code modification tool to a selected business area. Example choices for the business area include, but are not limited to, claims, eligibility management, enrollments and pre-authorizations/referrals. One or more of the ICD-10 codes to which any one ICD-9 code is mapped may apply to a plurality of different areas; in other words, an ICD-9 code contained in the codebase may map to an ICD-10 code that applies to multiple different business areas, e.g., to claims and enrollments. By selecting the "Selective Mapping" radio button 814 and then one of the business areas 1102, the modifications made to one or more lines of source code that contain ICD-9 codes which map to such an ICD-10 code will be made only with respect to the selected business areas and not to any of the other business areas. Thus, for example, if a particular ICD-10 code applies to both claims and enrollments, and the user selects "claims" in the business area user interface 1102, all modifications made by the source code modification tool to any line of source code containing an ICD-9 code that maps to that particular ICD-10 code will be made only with respect to claim and not with respect to enrollments.

Figure 12:
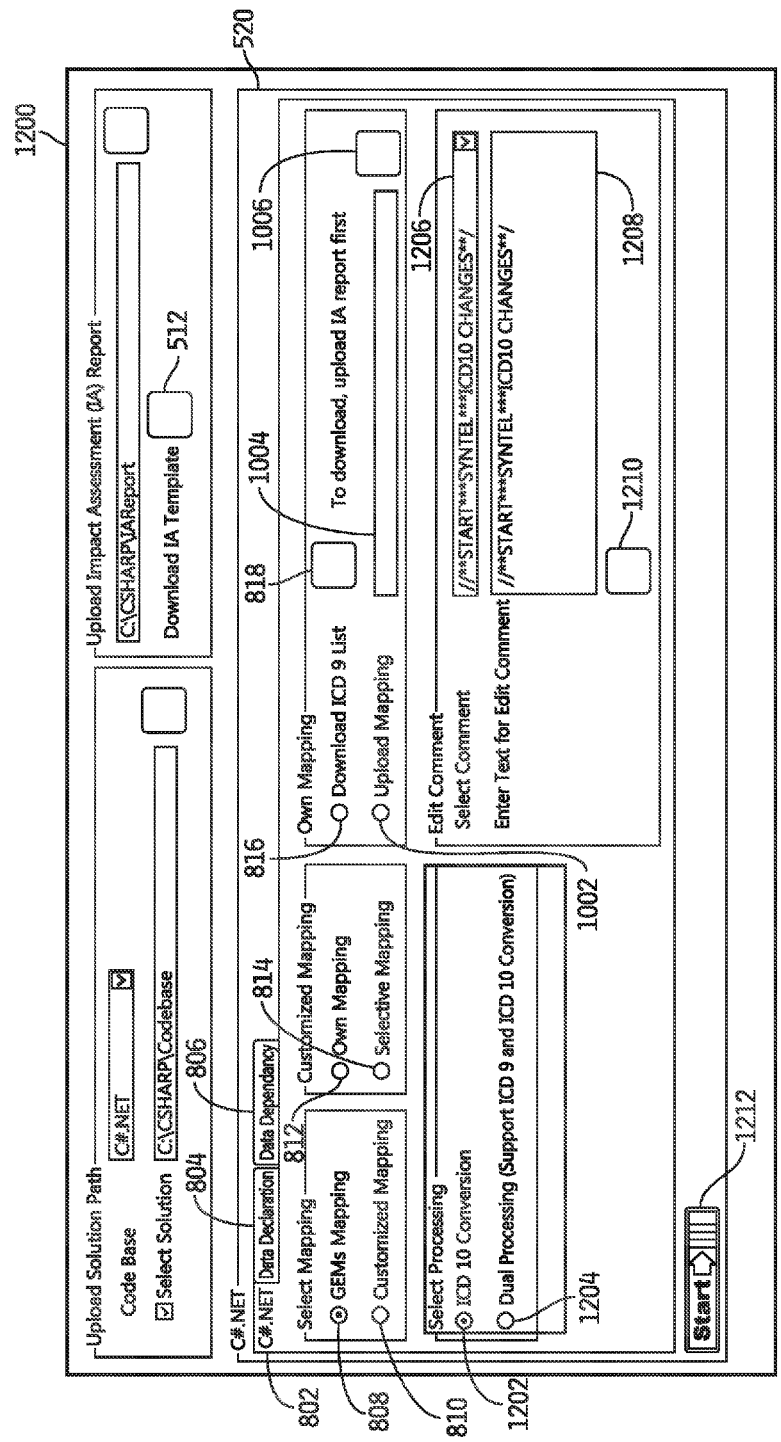
FIG. 12 is an example screen shot illustrating a process for selecting one or more code sets which will be supported by the selected codebase following modification thereof by the source code modification tool.

Referring now to FIG. 12, the tab 802 of the user interface 520 in the illustrated screen shot 1200 further illustratively includes additional features which may optionally be included in the source code modification tool. For example, the tab 802 may include a code processing selection interface including an ICD10 conversion radio button 1202 and a dual processing radio button 1204. If the user selects the ICD10 conversion button 1202, the source code modification tool will modify the source code by replacing each ICD-9 code contained in each impacted line of source code identified in the selected codebase impact assessment report with one of the plurality of ICD-9 to ICD-10 maps contained in the selected map file such that the modified lines of source code support the ICD-10 code set but not the ICD-9 code set. If, on the other hand, the user selects the dual processing button 1204, the source code modification tool will modify the source code by appending to each ICD-9 code contained in each impacted line of source code identified in the selected codebase impact assessment report one of the plurality of ICD-9 to ICD-10 maps contained in the selected map file such that the modified lines of source code support both the ICD-9 code set and the ICD-10 code set.

The source code modification tool illustratively includes one or more predefined comment lines with modifications made to each impacted line of source code. In one embodiment, for example, the source code modification tool adds one or a plurality of predefined comment lines just prior to each impacted line of source code modified by the source code modification tool, i.e., with no other lines of code between the one or more prior comment lines and the modified line of source code. In other embodiments, the source code modification tool may add one or a plurality of predefined comment lines just after each impacted line of source code modified by the source code modification tool, i.e., with no other lines of code between the modified line of source code and the one or more following comment lines. In still other embodiments, the source code modification tool may add one or a plurality of predefined comment lines both just prior and just after each impacted line of source code modified by the source code modification tool, i.e., with no other lines of source code between the one or more prior comment lines and the modified line of source code or between the modified line of source code and the one or more following comment lines.

The tab 802 may include a comment edit interface including a comment menu 1206, a selected comment edit field 1208 and a comment edit save button 1210. The user may, for example, select a comment line from the comment menu 1206, which may be any comment line in a plurality of comment lines to be added just prior to each modified source code line, or any comment line in a plurality of comment lines to be added just after each modified source code line. Upon selection, the selected comment line is inserted by the tool into the edit field 1208 where the user may make edits thereto. If the user thereafter selects the save button 1210, the tool will save the edited comment and include the edited comment in subsequent source code modifications.

The tab 802 further includes a start button 1212 which, upon selection or activation thereof by a user, causes the source code modification tool to automatically modify each impacted line of source code identified in the codebase impact assessment report by one or more of replacing at least one ICD-9 code with a selected, direct ICD-10 mapping, modifying at least one ICD-9 code with a corresponding ICD-10 code mapping while also retaining the ICD-9 code value to support both ICD-9 and ICD-10 code sets, modifying at least one data field length, adding at least one data field, renaming at least one data field, modifying at least one data type, modifying at least one logical expression, adding at least one data declaration, and adding at least one data movement instruction.

Figure 13:
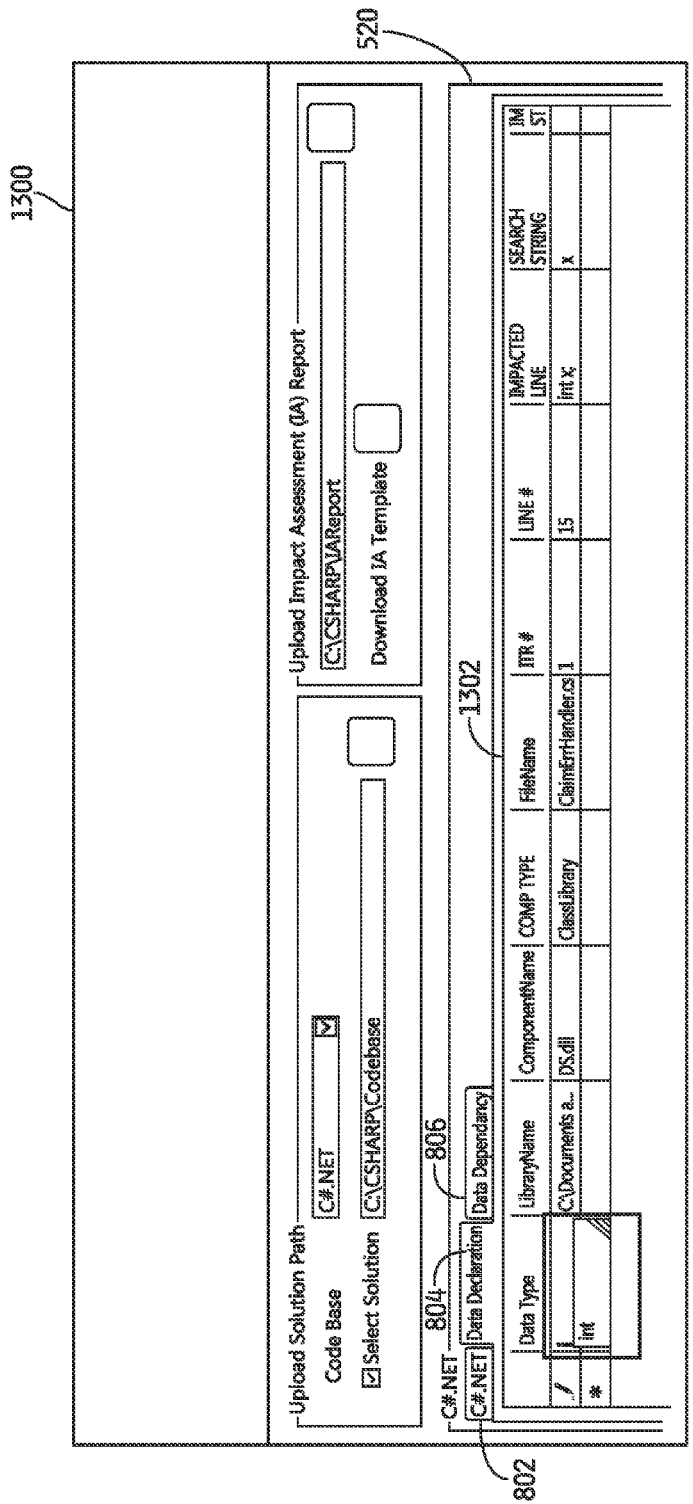
FIG. 13 is an example screen shot illustrating a process for including data declarations and/or data dependencies in the source code modification process carried out by the source code modification tool.

Referring now to FIG. 13, a screen shot 1300 is shown of the user interface 520 upon selection of the data declaration tab 804. As shown in the data declaration interface 1302 illustrated in FIG. 13, a user may modify the data type or data field, of one or more source code components for which the IA report contains data declaration statements, e.g., DS.dll in the illustrated example. A data dependency tab 806 may also or alternatively be selected within which the user may make similar such modifications. Any such data type or field length changes will be implemented in the corresponding impacted lines of source code in the codebase by the source code modification tool. The IA report may also contain other statements or information which identifies one or more lines of the source code as an impacted line that may require adding at least one data field, renaming at least one data field, modifying at least one logical expression, adding at least one data declaration, and/or adding at least one data movement instruction. Illustratively, although not required, the source code modification tool will also add comment lines, e.g., prior to and/or following, any such modified source code lines.

Figure 14:
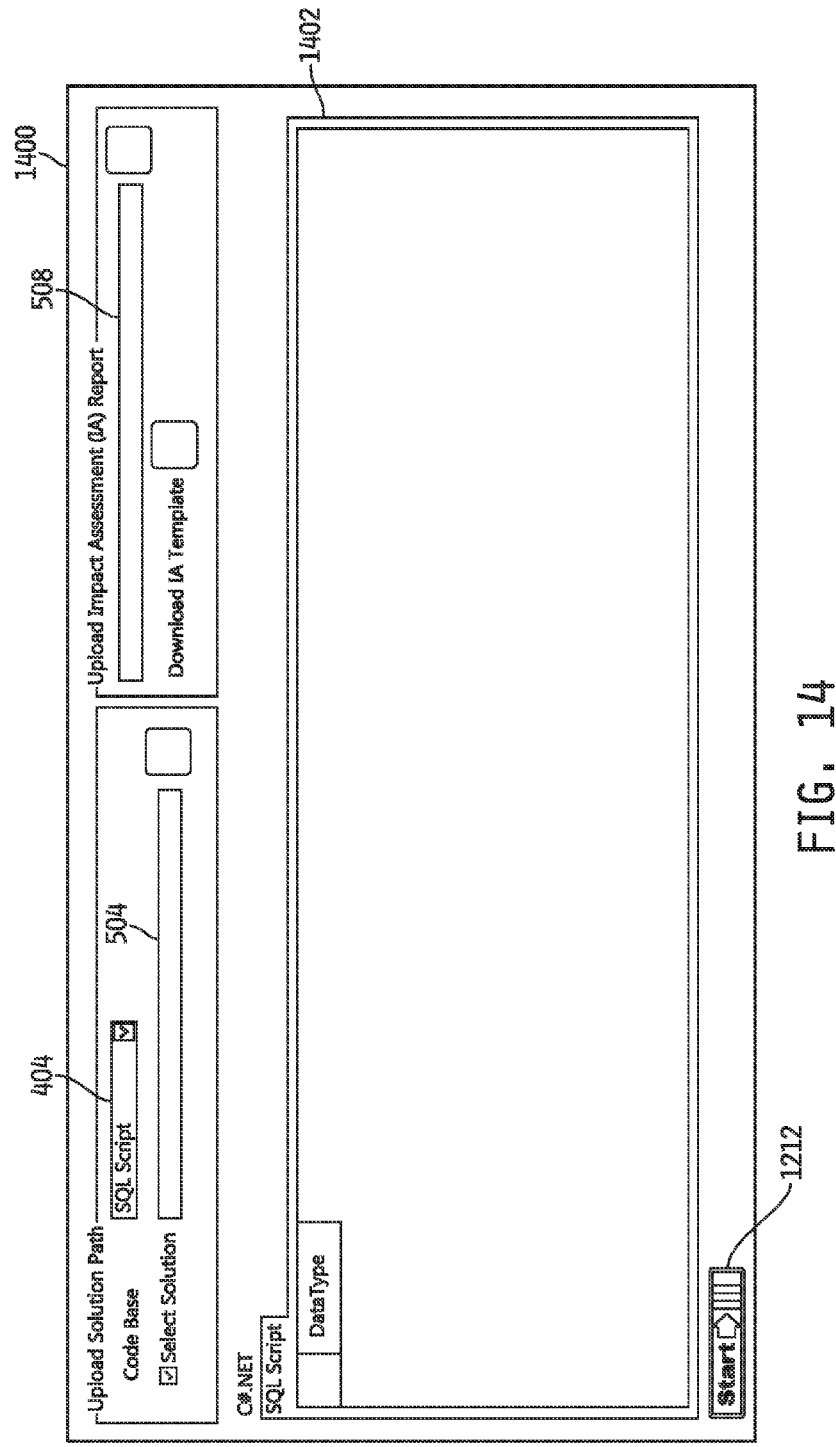
FIG. 14 is an example screen shot illustrating a process for selecting a codebase of another type for processing by the source code modification tool illustrated in FIGS. 2 and 3.
Figure 15:
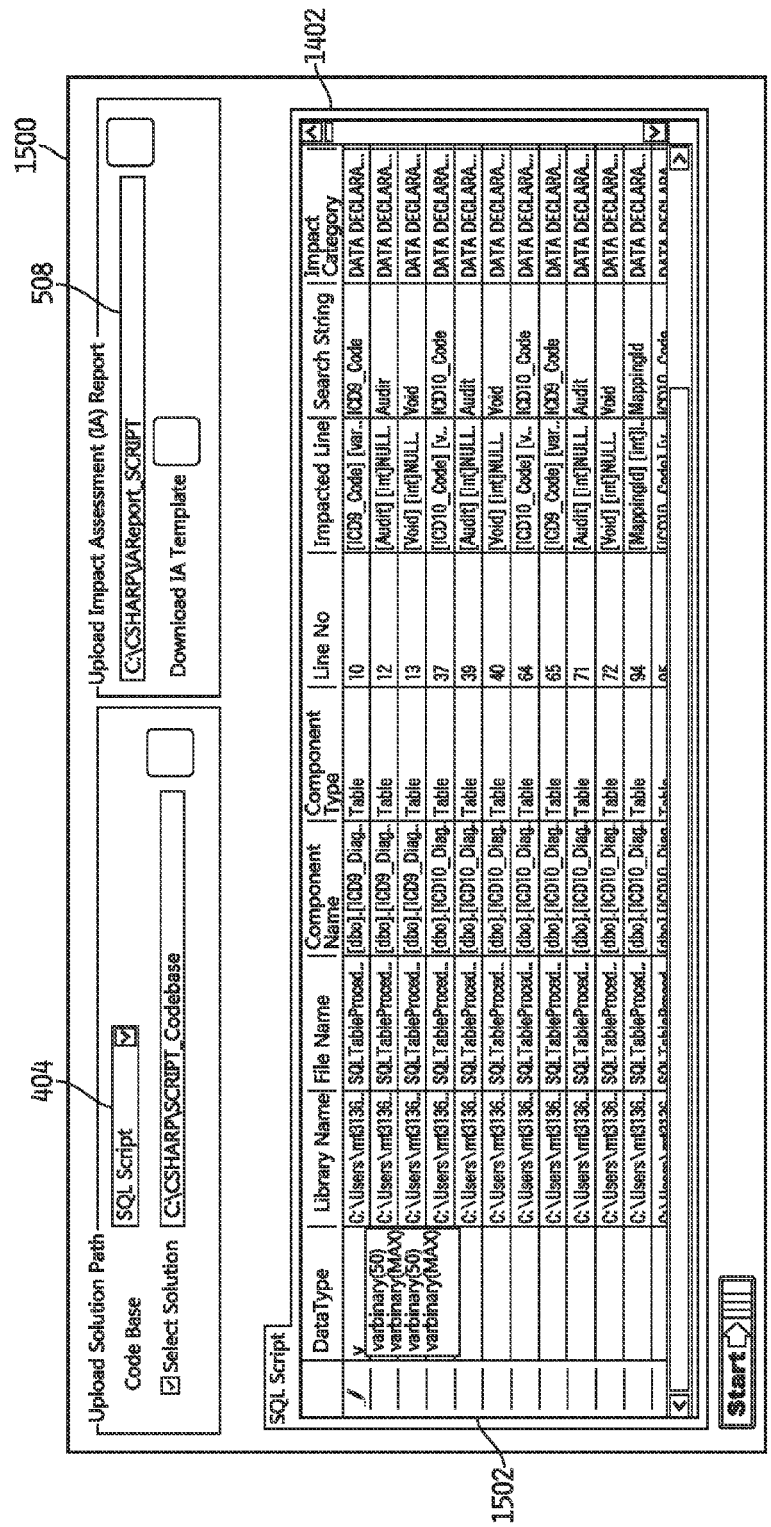
FIG. 15 is an example screen shot illustrating importation and display of a portion of the codebase selected using the process illustrated in FIG. 14.

Referring now to FIG. 14, a screen shot 1400 is shown of the main menu screen in which SQL Script has been selected in the codebase type menu 402. With the SQL Script codebase type selected, the screen shot 1400 illustrates a tool interface including the codebase solution input graphic 502 and the IA report input interface 508, as well as a user interface 1402 specific to SQL Script codebase types. With the IA report and the codebase identified, selected and input to the tool, the tool populates the user interface 1402 with a table 1502 of information from the selected IA report as illustrated in the screen shot 1500 of FIG. 15. As illustrated in the user interface 1402, the user can change the data type if the impact category is "data declaration." Other impact categories include "validation," "data movement" and "others" Any changes made to the IA report in relation to any such impacted category will be implemented in the corresponding impacted lines of source code in the codebase by the source code modification tool. Modifications made to the SQL Script codebase are implemented by the tool by modifying the script files to include ICD-9/ICD-10 code conversion scripts.

Referring now to FIG. 16, an example source code modification 1600 is shown in which the codebase is C#, and in which the source code modification made is the replacement of an ICD-9 code with a direct ICD-10 mapping, with comment lines before and after the modified source code line, such that the modified source code line supports only the mapped ICD-10 code and not the corresponding ICD-9 code. For C# and VB.NET codebase types, the tool illustratively creates an output library containing code conversion files, whereas for SQL Script codebase types the tool illustratively creates an output library containing code conversion script.

Referring to FIG. 17, an example source code modification 1700 is shown in which the codebase is VB.NET, and in which the source code modification made is by appending an ICD-10 code mapping to an ICD-9 code, with comment lines before and after the modified source code lines, such that the modified source code line supports both the ICD-9 code and the mapped ICD-10 code.

Referring to FIG. 18, an example source code modification 1800 is shown in which the codebase is VB.NET, and in which the source code modification made is a data movement and "others" with respect to a particular ICD-9 code, with comment lines before and after the modified source code lines.

Referring now to FIG. 19, an example source code modification 1900 is shown in which the codebase is SQL Script, and in which the source code modification made is the modification of a data field length, e.g., data field modified from 5 to 8, and with comment lines added before the modified source code line, such that the modified codebase supports only the ICD-10 code set.

While the disclosure has been illustrated and described in detail in the drawings and foregoing description, such an illustration and description is to be considered as exemplary and not restrictive in character, it being understood that only illustrative embodiments have been shown and described and that all changes and modifications consistent with the disclosure and recited claims are desired to be protected.

What is claimed is:

1. A system for automatically modifying source code to accommodate a software migration, the system comprising:
    a data management module configured to selectively receive a software codebase that supports international classification of diseases, ninth revision (ICD-9) codes and that contains a plurality of lines of source code, to selectively receive a codebase impact assessment report identifying each impacted line of the plurality of lines of source code in the codebase, each impacted line of the plurality of lines of source code requiring modification in order to support migration from ICD-9 codes to international classification of diseases, tenth revision (ICD-10) codes, and
    a codebase modification module responsive to activation thereof configured to automatically modify the codebase by modifying each impacted line of the plurality of lines of source code identified in the codebase impact assessment report so that the modified codebase supports migration from ICD-9 codes to ICD-10 codes, wherein the codebase modification module is configured to automatically modify at least one of the impacted lines of the plurality of lines of source code identified in the codebase impact assessment report by modifying at least one of a data field length, a data type and a logical expression in at least one of the impacted lines of the plurality of lines of source code identified in the codebase impact assessment report.

2. The system of claim 1, wherein the codebase modification module is configured to store at least the modified lines of source code in an electronic data storage.

3. The system of claim 1, wherein at least one of the impacted lines of the plurality of lines of source code contains an ICD-9 code, and wherein the codebase modification module is configured to automatically modify the at least one of the impacted lines of the plurality of lines of source code by replacing the ICD-9 code with at least one map that maps the ICD-9 code to one or more corresponding ICD-10 codes such that the modified codebase supports the one or more ICD-10 codes but does not support the ICD-9 code.

4. The system of claim 3, wherein the data management module is configured to selectively receive a map file containing the map.

5. The system of claim 1, wherein at least one of the impacted lines of the plurality of lines of source code contains an ICD-9 code, and wherein the codebase modification module is configured to automatically modify the at least one of the impacted lines of the plurality of lines of source code by appending at least one map to the ICD-9 code that maps the ICD-9 code to one or more corresponding ICD-10 codes such that the modified codebase supports the ICD-9 code and the one or more corresponding ICD-10 codes.

6. The system of claim 5, wherein the data management module is configured to selectively receive a map file containing the map.

7. The system of claim 1, wherein the codebase modification module is configured to automatically modify the codebase by inserting at least one comment line at least one of just prior to and just following each impacted line of the plurality of lines of source code.

8. The system of claim 1, wherein the codebase modification module is configured to automatically modify at least one of the impacted lines of the plurality of lines of source code identified in the codebase impact assessment report by adding at least one of a data field, a data declaration and a data movement instruction.

9. The system of claim 1, wherein the codebase modification module is configured to automatically modify at least one of the impacted lines of the plurality of lines of source code identified in the codebase impact assessment report by renaming at least one data field.

10. The system of claim 1, wherein at least one of the impacted lines of the plurality of lines of source code contains an ICD-9 code that maps to a particular ICD-10 code that applies to a plurality of different business areas of a healthcare system, and wherein the user interface module is configured to produce at least one graphic user interface for receiving user selection of one of the plurality of different business areas, and wherein the codebase modification module is configured to automatically modify the at least one of the impacted lines of the plurality of lines of source code by modifying the ICD-9 code with a map that maps the ICD-9 code to the ICD-10 code only with respect to the selected one of the plurality of different business areas.

11. The system of claim 1, wherein the codebase is one of a common language infrastructure (CLI) language codebase and a query language codebase.

12. A computerized method for automatically modifying source code to accommodate a software migration, the method comprising:
receiving by a processor a software codebase a software codebase that supports international classification of diseases, ninth revision (ICD-9) codes and that contains a plurality of lines of source code,
receiving by the processor a codebase impact assessment report identifying each impacted line of the plurality of lines of source code in the codebase, each impacted line of the plurality of lines of source code requiring modification in order to support migration from ICD-9 codes to international classification of diseases, tenth revision (ICD-10) codes, and
in response to a user input, automatically modifying the codebase with the processor by modifying each impacted line of the plurality of lines of source code identified in the codebase impact assessment report so that the modified codebase supports migration from ICD-9 codes to ICD-10 codes, wherein modifying each impacted line of the plurality of lines of source code comprises modifying at least one of the impacted lines of the plurality of lines of source code by at least one of modifying a data field length, a data type or a logical expression and adding at least one of a data field, a data declaration or a data movement instruction.

13. The computerized method of claim 12, wherein at least one of the impacted lines of the plurality of lines of source code contains an ICD-9 code, and wherein modifying each impacted line of the plurality of lines of source code comprises modifying the at least one of the impacted lines of the plurality of lines of source code by replacing the ICD-9 code with at least one map that maps the ICD-9 code to one or more corresponding ICD-10 codes such that the modified codebase supports the one or more ICD-10 codes but does not support the ICD-9 code.

14. The computerized method of claim 12, wherein at least one of the impacted lines of the plurality of lines of source code contains an ICD-9 code, and wherein modifying each impacted line of the plurality of lines of source code comprises modifying the at least one of the impacted lines of the plurality of lines of source code by appending to the ICD-9 code at least one map that maps the ICD-9 code to one or more corresponding ICD-10 codes such that the modified codebase supports the ICD-9 code and the one or more ICD-10 codes.

15. The computerized method of claim 12, wherein modifying each impacted line of the plurality of lines of source code comprises modifying at least one of the impacted lines of the plurality of lines of source code by inserting at least one comment line at least one of just prior to and just following the at least one of the impacted lines of the plurality of lines of source code.

16. The computerized method of claim 12, wherein at least one of the impacted lines of the plurality of lines of source code contains an ICD-9 code that maps to a particular ICD-10 code that applies to a plurality of different business areas of a healthcare system, and further comprising producing at least one graphic user interface for receiving user selection of one of the plurality of different business areas, and wherein modifying impacted lines of the plurality of lines of source code comprises modifying the at ICD-9 code contained in the least one of the impacted lines of the plurality of lines of source code with a map that maps the ICD-9 code to the ICD-10 code only with respect to the selected one of the plurality of different business areas.

17. The computerized method of claim 16, further comprising receiving a map file containing the map.

18. A computer program product comprising a non-transitory computer readable medium having instructions stored thereon which, when executed by at least one processor, cause the processor to:
receive a software codebase a software codebase that supports international classification of diseases, ninth revision (ICD-9) codes and that contains a plurality of lines of source code, receive a codebase impact assessment report identifying each impacted line of the plurality of lines of source code in the codebase, each impacted line of the plurality of lines of source code requiring modification in order to support migration from ICD-9 codes to international classification of diseases, tenth revision (ICD-10) codes, and
in response to a user input, automatically modify the codebase by modifying each impacted line of the plurality of lines of source code identified in the codebase impact assessment report so that the modified codebase supports migration from ICD-9 codes to ICD-10 codes, wherein modifying each impacted line of the plurality of lines of source code comprises modifying at least one of the impacted lines of the plurality of lines of source code by at least one of modifying a data field length, a data type or a logical expression and adding at least one of a data field, a data declaration or a data movement instruction.

* * * * *

UNITED STATES PATENT AND TRADEMARK OFFICE
CERTIFICATE OF CORRECTION

| | |
|---|---|
| PATENT NO. | : 9,268,907 B2 |
| APPLICATION NO. | : 14/306026 |
| DATED | : February 23, 2016 |
| INVENTOR(S) | : Murlidhar Reddy |

Page 1 of 1

It is certified that error appears in the above-identified patent and that said Letters Patent is hereby corrected as shown below:

In the Claims:

Column 16, line 40 (Claim 16), delete "impacted lines" and insert --each impacted line--

Column 16, line 41 (Claim 16), before "ICD-9" delete "at"

Column 16, line 52 (Claim 18), delete "receive a software codebase a software codebase" and insert --receive a software codebase--

Signed and Sealed this
Third Day of May, 2016

Michelle K. Lee
*Director of the United States Patent and Trademark Office*